(12) United States Patent
Parker et al.

(10) Patent No.: US 9,872,990 B2
(45) Date of Patent: *Jan. 23, 2018

(54) METHOD AND APPARATUS FOR APPLICATION OF A NEURAL STIMULUS

(71) Applicant: Saluda Medical Pty Limited, Artarmon, NSW (AU)

(72) Inventors: John Louis Parker, Artarmon (AU); James Hamilton Laird-Wah, Artarmon (AU)

(73) Assignee: Saluda Medical Pty Limited, Artarmon (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,929

(22) Filed: Sep. 3, 2015

(65) Prior Publication Data

US 2015/0374999 A1 Dec. 31, 2015
US 2017/0001017 A9 Jan. 5, 2017

Related U.S. Application Data

(63) Continuation of application No. 14/117,586, filed as application No. PCT/UA2012/000515 on May 11, 2012, now Pat. No. 9,155,892.

(30) Foreign Application Priority Data

May 13, 2011 (AU) ................................ 2011901828
May 13, 2011 (AU) ................................ 2011901829

(51) Int. Cl.
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/36071* (2013.01); *A61N 1/36167* (2013.01)

(58) Field of Classification Search
None
See application file for complete search history.

(56) References Cited

U.S. PATENT DOCUMENTS 3,817,254 A 6/1974 Maurer
4,418,695 A 12/1983 Buffet
(Continued)

FOREIGN PATENT DOCUMENTS

EP 0219084 4/1987
EP 2019716 A 11/2007
(Continued)

OTHER PUBLICATIONS

Mahnam A, Hashemi SM, Grill WM. Measurement of the current-distance relationship using a novel refractory interaction technique. J Neural Eng. Jun. 2009;6(3):036005.*
(Continued)

*Primary Examiner* — Ankit D Tejani
(74) *Attorney, Agent, or Firm* — KPPB LLP (57) ABSTRACT

A method of applying a neural stimulus with an implanted electrode array involves applying a sequence of stimuli configured to yield a therapeutic effect while suppressing psychophysical side effects. The stimuli sequence is configured such that a first stimulus recruits a portion of the fibre population, and a second stimulus is delivered within the refractory period following the first stimulus and the second stimulus being configured to recruit a further portion of the fibre population. Using an electrode array and suitable relative timing of the stimuli, ascending or descending volleys of evoked responses can be selectively synchronised or desynchronised to give directional control over responses evoked.

14 Claims, 6 Drawing Sheets

(56) References Cited

U.S. PATENT DOCUMENTS

| | | | |
|---|---|---|---|
| 4,474,186 A | 10/1984 | Ledley et al. | |
| 4,628,934 A | 12/1986 | Pohndorf et al. | |
| 4,807,643 A | 2/1989 | Rosier | |
| 4,856,525 A | 8/1989 | Van Den et al. | |
| 5,113,859 A | 5/1992 | Funke | |
| 5,139,020 A | 8/1992 | Koestner et al. | |
| 5,143,081 A | 9/1992 | Young et al. | |
| 5,156,154 A | 10/1992 | Valenta, Jr. et al. | |
| 5,172,690 A | 12/1992 | Nappholz et al. | |
| 5,184,615 A | 2/1993 | Nappholz et al. | |
| 5,188,106 A | 2/1993 | Nappholz et al. | |
| 5,215,100 A | 6/1993 | Spitz | |
| 5,324,311 A | 6/1994 | Acken | |
| 5,417,719 A | 5/1995 | Hull et al. | |
| 5,431,693 A | 7/1995 | Schroeppel | |
| 5,458,623 A | 10/1995 | Lu et al. | |
| 5,476,486 A | 12/1995 | Lu et al. | |
| 5,497,781 A | 3/1996 | Chen et al. | |
| 5,638,825 A | 6/1997 | Yamazaki et al. | |
| 5,702,429 A | 12/1997 | King et al. | |
| 5,758,651 A | 6/1998 | Nygard et al. | |
| 5,776,170 A | 7/1998 | Macdonald et al. | |
| 5,785,651 A | 7/1998 | Kuhn et al. | |
| 5,792,212 A | 8/1998 | Weijand et al. | |
| 5,814,092 A | 9/1998 | King | |
| 5,913,882 A | 6/1999 | King | |
| 5,999,848 A | 12/1999 | Gord et al. | |
| 6,027,456 A | 2/2000 | Feler et al. | |
| 6,038,480 A | 3/2000 | Hrdlicka et al. | |
| 6,066,163 A | 5/2000 | John | |
| 6,114,164 A | 9/2000 | Dennis et al. | |
| 6,144,881 A | 11/2000 | Hemming et al. | |
| 6,157,861 A | 12/2000 | Faltys et al. | |
| 6,212,431 B1 | 4/2001 | Hahn et al. | |
| 6,246,912 B1 | 6/2001 | Sluijter et al. | |
| 6,381,496 B1 | 4/2002 | Meadows et al. | |
| 6,463,328 B1 | 10/2002 | John | |
| 6,473,649 B1 | 10/2002 | Gryzwa et al. | |
| 6,473,653 B1 | 10/2002 | Schallhorn et al. | |
| 6,493,576 B1 | 12/2002 | Dankwart-Eder | |
| 6,522,932 B1 | 2/2003 | Kuzma | |
| 6,600,955 B1 | 7/2003 | Zierhofer et al. | |
| 6,658,293 B2 | 12/2003 | Vonk et al. | |
| 6,675,046 B2 | 1/2004 | Holsheimer | |
| 6,782,292 B2 | 8/2004 | Whitehurst | |
| 6,898,582 B2 | 5/2005 | Lange et al. | |
| 7,089,059 B1 * | 8/2006 | Pless | A61B 5/0484 607/45 |
| 7,171,261 B1 | 1/2007 | Litvak et al. | |
| 7,231,254 B2 | 6/2007 | DiLorenzo et al. | |
| 7,286,876 B2 | 10/2007 | Yonce et al. | |
| 7,412,287 B2 | 8/2008 | Yonce et al. | |
| 7,450,992 B1 | 11/2008 | Cameron | |
| 7,734,340 B2 | 6/2010 | De | |
| 7,742,810 B2 | 6/2010 | Moffitt | |
| 7,792,584 B2 | 9/2010 | Van Oort et al. | |
| 7,818,052 B2 | 10/2010 | Litvak et al. | |
| 7,835,804 B2 | 11/2010 | Fridman et al. | |
| 8,224,459 B1 | 7/2012 | Pianca et al. | |
| 8,239,031 B2 | 8/2012 | Fried et al. | |
| 8,359,102 B2 | 1/2013 | Thacker et al. | |
| 8,494,645 B2 | 7/2013 | Spitzer et al. | |
| 8,588,929 B2 | 11/2013 | Davis et al. | |
| 9,155,892 B2 | 10/2015 | Parker et al. | |
| 9,381,356 B2 | 7/2016 | Parker et al. | |
| 9,386,934 B2 | 7/2016 | Parker et al. | |
| 2003/0045909 A1 | 3/2003 | Gross et al. | |
| 2003/0139781 A1 | 7/2003 | Bradley et al. | |
| 2003/0195580 A1 | 10/2003 | Bradley et al. | |
| 2004/0088017 A1 | 5/2004 | Sharma et al. | |
| 2004/0122482 A1 | 6/2004 | Tung et al. | |
| 2004/0158298 A1 | 8/2004 | Gliner | |
| 2004/0225211 A1 | 11/2004 | Gozani et al. | |
| 2004/0254494 A1 | 12/2004 | Spokoyny et al. | |
| 2005/0010265 A1 | 1/2005 | Baru Fassio | |
| 2005/0021104 A1 | 1/2005 | DiLorenzo | |
| 2005/0065427 A1 | 3/2005 | Magill | |
| 2005/0070982 A1 | 3/2005 | Heruth et al. | |
| 2005/0075683 A1 | 4/2005 | Miesel et al. | |
| 2005/0101878 A1 | 5/2005 | Daly | |
| 2005/0137670 A1 | 6/2005 | Christopherson et al. | |
| 2005/0149154 A1 | 7/2005 | Cohen | |
| 2005/0203600 A1 | 9/2005 | Wallace | |
| 2005/0209655 A1 | 9/2005 | Bradley et al. | |
| 2005/0282149 A1 | 12/2005 | Kovacs et al. | |
| 2006/0009820 A1 | 1/2006 | Royle et al. | |
| 2006/0020291 A1 | 1/2006 | Gozani | |
| 2006/0135998 A1 | 6/2006 | Libbus et al. | |
| 2006/0195159 A1 | 8/2006 | Bradley et al. | |
| 2006/0212089 A1 | 9/2006 | Tass | |
| 2006/0217782 A1 | 9/2006 | Boveja et al. | |
| 2006/0287609 A1 | 12/2006 | Litvak et al. | |
| 2007/0073354 A1 | 3/2007 | Knudson et al. | |
| 2007/0100378 A1 | 5/2007 | Maschino | |
| 2007/0178579 A1 | 8/2007 | Ross et al. | |
| 2007/0208394 A1 | 9/2007 | King et al. | |
| 2007/0225767 A1 | 9/2007 | Daly | |
| 2007/0244410 A1 | 10/2007 | Fridman | |
| 2007/0250120 A1 | 10/2007 | Flach et al. | |
| 2007/0255372 A1 | 11/2007 | Metzler et al. | |
| 2007/0282217 A1 | 12/2007 | McGinnis et al. | |
| 2007/0287931 A1 | 12/2007 | Dilorenzo | |
| 2008/0021292 A1 | 1/2008 | Stypulkowski | |
| 2008/0051647 A1 | 2/2008 | Wu et al. | |
| 2008/0097529 A1 | 4/2008 | Parramon et al. | |
| 2008/0147155 A1 | 6/2008 | Swoyer | |
| 2008/0183076 A1 | 7/2008 | Witte | |
| 2008/0234780 A1 * | 9/2008 | Smith | A61N 1/36139 607/45 |
| 2008/0275527 A1 | 11/2008 | Greenberg et al. | |
| 2008/0294221 A1 | 11/2008 | Kilgore | |
| 2008/0300655 A1 | 12/2008 | Cholette et al. | |
| 2009/0033486 A1 | 2/2009 | Costantino et al. | |
| 2009/0157155 A1 | 6/2009 | Bradley | |
| 2009/0270957 A1 | 10/2009 | Pianca | |
| 2009/0287277 A1 | 11/2009 | Conn et al. | |
| 2009/0299214 A1 | 12/2009 | Wu et al. | |
| 2009/0306491 A1 | 12/2009 | Haggers | |
| 2010/0010388 A1 | 1/2010 | Panken et al. | |
| 2010/0058126 A1 | 3/2010 | Chang et al. | |
| 2010/0069835 A1 | 3/2010 | Parker | |
| 2010/0069996 A1 | 3/2010 | Strahl | |
| 2010/0070007 A1 | 3/2010 | Parker | |
| 2010/0070008 A1 | 3/2010 | Parker | |
| 2010/0106231 A1 | 4/2010 | Torgerson | |
| 2010/0114258 A1 | 5/2010 | Donofrio et al. | |
| 2010/0125313 A1 | 5/2010 | Lee et al. | |
| 2010/0125314 A1 | 5/2010 | Bradley et al. | |
| 2010/0145222 A1 | 6/2010 | Brunnett et al. | |
| 2010/0179626 A1 | 7/2010 | Pilarski | |
| 2010/0191307 A1 * | 7/2010 | Fang | A61N 1/0551 607/46 |
| 2010/0222844 A1 | 9/2010 | Troosters et al. | |
| 2010/0222858 A1 | 9/2010 | Meloy | |
| 2010/0249643 A1 | 9/2010 | Gozani | |
| 2010/0249867 A1 | 9/2010 | Wanasek | |
| 2010/0258342 A1 | 10/2010 | Parker | |
| 2010/0262208 A1 | 10/2010 | Parker | |
| 2010/0262214 A1 | 10/2010 | Robinson | |
| 2010/0280570 A1 | 11/2010 | Sturm et al. | |
| 2010/0286748 A1 | 11/2010 | Midani et al. | |
| 2010/0331604 A1 | 12/2010 | Okamoto et al. | |
| 2010/0331926 A1 | 12/2010 | Lee et al. | |
| 2011/0021943 A1 | 1/2011 | Lacour et al. | |
| 2011/0087085 A1 | 4/2011 | Tsampazis et al. | |
| 2011/0093042 A1 | 4/2011 | Torgerson et al. | |
| 2011/0106100 A1 | 5/2011 | Bischoff | |
| 2011/0184488 A1 | 7/2011 | De et al. | |
| 2011/0224749 A1 | 9/2011 | Ben-David et al. | |
| 2011/0313310 A1 | 12/2011 | Tomita | |
| 2011/0313483 A1 | 12/2011 | Hincapie et al. | |
| 2012/0029377 A1 | 2/2012 | Polak | |
| 2012/0109236 A1 | 5/2012 | Jacobson et al. | |
| 2012/0253423 A1 | 10/2012 | Youn et al. | |

(56) References Cited

U.S. PATENT DOCUMENTS

| | | |
|---|---|---|
| 2012/0277621 A1 | 11/2012 | Gerber et al. |
| 2012/0277823 A1 | 11/2012 | Gerber et al. |
| 2013/0289661 A1 | 10/2013 | Griffith et al. |
| 2013/0289683 A1 | 10/2013 | Parker et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243931 A1 | 8/2014 | Parker et al. |
| 2014/0276195 A1 | 9/2014 | Papay et al. |
| 2014/0277250 A1 | 9/2014 | Su et al. |
| 2014/0288577 A1 | 9/2014 | Robinson et al. |
| 2015/0164354 A1 | 6/2015 | Parker et al. |
| 2015/0174396 A1 | 6/2015 | Fisher et al. |
| 2015/0238304 A1 | 8/2015 | Lamraoui |
| 2015/0282725 A1 | 10/2015 | Single |
| 2015/0313487 A1 | 11/2015 | Single |
| 2016/0166164 A1 | 6/2016 | Obradovic et al. |
| 2016/0287126 A1 | 10/2016 | Parker et al. |
| 2016/0287182 A1 | 10/2016 | Single |
| 2017/0049345 A1 | 2/2017 | Single |
| 2017/0071490 A1 | 3/2017 | Parker et al. |
| 2017/0135624 A1 | 5/2017 | Parker |

FOREIGN PATENT DOCUMENTS

| | | |
|---|---|---|
| EP | 2243510 A2 | 10/2010 |
| EP | 2443995 A2 | 4/2012 |
| WO | 1983003191 A | 9/1983 |
| WO | 1993001863 A1 | 2/1993 |
| WO | 9612383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003043690 | 5/2003 |
| WO | 2003103484 | 12/2003 |
| WO | 2004021885 A1 | 3/2004 |
| WO | 20040103455 | 12/2004 |
| WO | 2005032656 A1 | 4/2005 |
| WO | 2005105202 A1 | 11/2005 |
| WO | 2006091636 A2 | 8/2006 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015143509 A1 | 10/2015 |
| WO | 2015168735 A1 | 11/2015 |
| WO | 2016011512 | 1/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |

OTHER PUBLICATIONS

European Search Report for European Application 12785619.3 Search Completed Oct. 13, 2014, dated Oct. 23, 2014, 7 pgs.

European Search Report for European Application 12785669.8 Search Completed Sep. 22, 2014, dated Sep. 29, 2014, 5 pgs.

Extended European Search Report for EP Application 12785483.4 completed Sep. 16, 2014, 7 pgs.

International Search Report for Australian Application 2011901829 Search Completed Feb. 6, 2012, dated Feb. 7, 2012, 3pgs.

International Search Report for International Application No. PCT/AU2012/000511, International Filing Date May 11, 2012, Search Completed May 17, 2012, dated May 18, 2012, 4 pgs.

International Search Report for International Application No. PCT/AU2012/000512, International Filing Date May 11, 2012, Search Completed Jul. 10, 2012, dated Jul. 11, 2012, 4 pgs.

International Search Report for International Application No. PCT/AU2012/000513, International Filing Date May 11, 2012, Search Completed May 29, 2012, dated May 30, 2012, 5 pgs.

International Search Report for International Application No. PCT/AU2012/000515, International Filing Date May 11, 2012, Search Completed May 21, 2012, dated Jun. 4, 2012, 5 pgs.

International Search Report for International Application No. PCT/AU2012/000516, International Filing Date May 11, 2012, Search Completed Jul. 11, 2012, dated Jul. 12, 2012, 8 pgs.

International Search Report for International Application No. PCT/AU2012/000517, International Filing Date May 11, 2012, Search Completed Jun. 4, 2012, dated Jun. 6, 2012, 3 pgs.

International Search Report for International Application No. PCT/AU2012/000518, International Filing Date May 11, 2012, Search Completed Jun. 8, 2012, dated Jun. 12, 2012, 4 pgs.

Written Opinion for International Application No. PCT/AU2012/000511, International Filing Date May 11, 2012, Search Completed May 17, 2012, dated May 18, 2012, 5 pgs.

Written Opinion for International Application No. PCT/AU2012/000512, International Filing Date May 11, 2012, Search Completed Jul. 10, 2012, dated Jul. 11, 2012, 7 pgs.

Written Opinion for International Application No. PCT/AU2012/000513, International Filing Date May 11, 2012, Search Completed May 29, 2012, dated May 30, 2012, 7 pgs.

Written Opinion for International Application No. PCT/AU2012/000515, International Filing Date May 11, 2012, Search Completed May 21, 2012, dated Jun. 4, 2012, 4 pgs.

Written Opinion for International Application No. PCT/AU2012/000516, International Filing Date May 11, 2012, Search Completed Jul. 11, 2012, dated Jul. 12, 2012, 8 pgs.

Written Opinion for International Application No. PCT/AU2012/000517, International Filing Date May 11, 2012, Search Completed Jun. 4, 2012, dated Jun. 6, 2012, 5 pgs.

Written Opinion for International Application No. PCT/AU2012/000518, International Filing Date May 11, 2012, Search Completed Jun. 8, 2012, dated Jun. 12, 2012, 10 pgs.

Andreassen, S. et al., "Muscle Fibre Conduction Velocity in Motor Units of the Human Anterior Tibial Muscle: a New Size Principle Parameter", J. Physiol, (1987), 391, pp. 561-571.

Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.

Borg et al., "Conduction velocity and refractory period of single motor nerve fibres in antecedent poliomyelitis", Journal of Neurology, Neurosurgery, and Psychiatry, vol. 50, 1987, 443-446.

(56) References Cited

OTHER PUBLICATIONS

Dawson, G. D., "The relative excitability and conduction velocity of sensory and motor nerve fibres in man", Journal of Physiology, 1956, vol. 131(2), pp. 436-451. Figs. 1-5; Table 1; p. 437 "Methods"; pp. 438-447 "Results".

Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. p. 324 section 'Paraesthesia Coverage by Dermatome,' p. 326 section 'Total Paraesthesia Coverage' and Figures 1 and 6-10.

Dillier, N. et al., "Measurement of the electrically evoked compound action potential via a neural response telemetry system", Ann. Otol. Rhinol. Laryngol. 111 (May 2002), No. 5, pp. 407-414. Abstract & Figures 2-3, 407-414.

Fagius, J. et al., "Sympathetic Reflex Latencies and Conduction Velocities in Normal Man", Journal of Neurological Sciences, 1980. vol. 47, pp. 433-448.

Goodall, E. V., "Modeling Study of Activation and Propagation delays During Stimulation of Peripheral Nerve Fibres with a Tripolar Cuff Electrode", IEEE Trans.Rehab.Eng. v 3, pp. 272-282.

Harper, A. A. et al., "Conduction Velocity is Related to Morphological Cell Type in Rat Dorsal Root Ganglion Neurones", J. Physiol, (1985), 359, pp. 31-46.

Kent et al., "Instrumentation to Record Evoked Potentials for Closed-Loop Control of Deep Brain Stimulation", Conf. Proc. IEEE Eng. Med Biol. Sol, Aug. 2012, 10 pgs.

Mahnam, A. et al., "Measurement of the current-distance relationship using a novel refractory interaction technique", J. Neural Eng. 6 (2009), pp. 036005 (published May 20, 2009) Abstract, Sec. 2.2 & Figure 2b, 036005.

Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.

McGill, Kevin et al., "On the Nature and Elimination of Stimulus Artifact in Nerve Signals Evoked and Recorded Using Surgace Electrodes", IEEE Transactions on Biomedical Engineering, vol. BME-29, No. 2, Feb. 1982, pp. 129-137.

Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.

Orstavik, Kristin et al., "Pathological C-fibres in patients with a chronic painful condition", Brain (2003), 126, 567-578.

Parker, J. L. et al., "Compound Action Potentials Recorded in the Human Spinal Cord During Neurostimulation for Pain Relief", Pain, vol. 153, 2012, pp. 593-601.

Roy, S. H. et al, "Effects of Electrode Location on Myoelectric Conduction Velocity and Median Frequency Estimates", J. Appl. Physiol. 61 (4), 1986, pp. 1510-1517.

Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.

Yearwood, T. L., "Pulse Width Programming in Spinal Cord Stimulation: a Clinical Study", Pain Physician. 2010. vol. 13, pp. 321-335.

Yuan, S. et al., "Recording monophasic action potentials using a platinum-electrode ablation catheter", Europace. Oct. 2000; 2(4):312-9; Abstract.

Extended European Search Report for European Application No. 11820923.8, report completed Dec. 9, 2013, report dated Dec. 17, 2013, 6 pgs.

Extended European Search Report for European Application No. 13852669.4, Search completed Jun. 8, 2016, dated Jun. 22, 2016, 9 pgs.

Extended European Search Report for European Application No. 14861553.7, Search completed Jun. 8, 2017, dated Jun. 19, 2017, 8 pgs.

Extended European Search Report for European Application No. 14863597.2, Search completed Jun. 6, 2017, dated Jun. 13, 2017, 9 pgs.

Extended European Search Report for European Application No. 13853514.1, Search completed Jun. 8, 2016, dated Jun. 15, 2016, 07 pgs.

International Preliminary Report on Patentability for International Application No. PCT/AU2012/001441, Report dated May 27, 2014, 10 pgs.

International Search Report and Written Opinion for International Application No. PCT/AU2011/001127, date completed Nov. 11, 2011, dated Nov. 15, 2011, 13 pgs.

International Search Report and Written Opinion for International Application No. PCT/AU2012/001441, International Filing Date Nov. 23, 2012, Search Completed Feb. 26, 2013, dated Feb. 26, 2013, 14 pgs.

International Search Report and Written Opinion for International Application No. PCT/AU2014/001049, Search completed Feb. 10, 2015, dated Feb. 10, 2015, 8 pgs.

International Search Report and Written Opinion for International Application No. PCT/AU2014/050369, Search completed Feb. 20, 2015, dated Feb. 20, 2015, 14 pgs.

International Search Report and Written Opinion for International Application No. PCT/AU2015/050135, Search completed Jun. 30, 2015, dated Jun. 30, 2015, 26 pgs.

International Search Report and Written Opinion for International Application No. PCT/AU2015/050422, Search completed Oct. 14, 2015, dated Oct. 14, 2015, 17 pgs.

International Search Report and Written Opinion for International Application No. PCT/AU2015/050724, Search completed May 9, 2016, dated May 9, 2016, 8 pgs.

International Search Report and Written Opinion for International Application No. PCT/AU2015/050753, Search completed Feb. 10, 2016, dated Feb. 10, 2016, 10 pgs.

International Search Report and Written Opinion for International Application No. PCT/AU2015/050787, Search completed Mar. 16, 2016, dated Mar. 16, 2016, 10 pgs.

International Search Report and Written Opinion for International Application No. PCT/AU2016/050019, Search completed May 4, 2016, dated May 4, 2016, 16 pgs.

International Search Report and Written Opinion for International Application No. PCT/AU2015/050215, Search completed Jul. 30, 2015, dated Jul. 30, 2015, 8 pgs.

Medtronic, Spinal Cord Stimulation, RestoreSensor Neurostimulator, Features and Specification: Specification, Printed Jun. 16, 2014, 2 pgs.

Medtronic, Spinal Cord Stimulation, RestoreSensor Neurostimulator, Features and Specification: Summary Printed Jun. 16, 2014, 1 pg.

Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.

"Advanced Pain Therapy using Neurostimulation for Chronic Pain", Medtronic RestoreSensor clinical trial paper, Clinical summary, 2011-11, pp. 32.

"Battelle Neurotechnology—Moving Beyond the Limits in Neurotechnology", Battelle, www.battelle.org, May 2014, pp. 1-2.

"Haptic technology", Wikipedia, Retrieved from: http://en.wikipedia.org/wiki/Haptic_technology, Last modified on Sep. 15, 2014, Printed on Sep. 15, 2014, 5 pgs.

"Implants for surgery, Cardiac pacemakers", IS-1 standard ISO 5841-3-2000, Oct. 15, 2000.

"International Search Report", International Search Report & Written Opinion for International Application No. PCT/AU2013/001280, Search Completed Jan. 16, 2014, dated Jan. 16, 2014, 8 pgs.

"International Search Report", International Search Report & Written Opinion for International Application PCT/AU2013/001279, Search Completed Jan. 9, 2014, dated Jan. 9, 2014, 9 pgs.

(56) References Cited

OTHER PUBLICATIONS

"Neural Bypass Technology Enables Movement in Paralyzed Patient", Posted on Jul. 29, 2014, 6 a.m. in Brain chips/computer interface, pp. 1-2.

"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.

"Wide bandwidth BioAmplifier", http://www.psylab.com/html/default_bioamp.htm, Printed Jan. 30, 2014, 1-3 pages.

Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.

Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.

Brown et al., "Impact of Deep Brain Stimulation on Upper Limb Askinesia in Parkingson's Disease", Annals of Neurology, 45, No. 4, 1999, pp. 473-488.

Budagavi et al., "Modelling of compound nerve action potentials health and disease", Engineering in Medicine and Biology Society, 1992 14th Annual International Conference of the IEEE. vol. 6. IEEE, 1992. pp. 2600-2601.

Coquery et al., "Backward and forward masking in the perception of cutaneous stimuli", Perception & Psychophysics, 1973, vol. 13.No. 2, pp. 161-163.

Devergnas et al., A, "Cortical potentials evoked by deep brain stimulation in the subthalamic area", Front Syst Neurosci. 2011; 5: 30. May 13, 2011. doi:10.3389/fnsys.2011.00030.

Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.

England et al., "Increased Numbers of Sodium Channels Form Along Demyelinated Axons", Brain Research 548, No. 1-2 (May 10, 1991): 334-337.

Falowski et al., "Spinal Cord Stimulation: an update", Neurotherapeutics: The Journal of the American Society for Experimental NeuroTherapeutics 5, No. 1, Jan. 2008, pp. 86-99.

Franke et al., Felix, "An Online Spike Detection and Spike Classification Algorithm Capable of Instantaneous Resolution of Overlapping Spikes", Journal of Computational Neuroscience, 2010, vol. 29, No. 1-2, pp. 127-148.

Fuentes et al., "Spinal Cord Stimulation Restores Locomotion in Animal Models of Parkinson's Disease", Science, vol. 323, No. 5921, Mar. 20, 2009, pp. 1578-1582.

George et al., "Vagus nerve stimulation: a new tool for brain research and therapy", Biological Psychiatry 47, No. 4, Feb. 15, 2000, pp. 287-295.

Gorman et al., "ECAP Mapping of the Spinal Cord: Influence of Electrode Position on Aβ Recruitment", (2012). In 16th Annual Meeting. Presented at the North American Neuromodulation Society, Las Vegas, NV.

Gorman et al., "Neural Recordings for Feedback Control of Spinal Cord Stimulation: Reduction of Paresthesia Variability", 2013, In International Neuromodulation Society 11th World Congress. Presented at the International Neuromodulation Society 11th World Congress, Berlin, Germany.

Hallstrom et al, "Distribution of lumbar spinal evoked potentials and their correlation with stimulation-induced paresthesiae", (1991), Electroencephalography and clinical neurophysiology 80:126-139.

Holsheimer et al., "Optimum Electrode Geometry for Spinal Cord Stimulation: the Narrow Bipole and Tripole", Medical and Biological Engineering and Computing, 35, No. 5, 1997, pp. 493-497.

Huff, Terry B. et al., "Real-Time CARS Imaging Reveals a Calpain-Dependent Pathway for Paranodal Myelin Retraction during High-Frequency Stimulation", PLoS One vol. 6, issue 3 (Mar. 3, 2011): e17176, 11 pgs.

Hui, Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Kent et al., AR, "Recording evoked potentials during deep brain stimulation: development and validation of instrumentation to suppress the stimulus artefact", J Neural Eng. Jun. 2012; 9 (3):036004, Apr. 18, 2012, doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.

Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.

Krames et al., "Neuromodulation", 1st Edition, Academic Press, 2009, p. 540-541.

Krarup, Christian, "Compound sensory action potential in normal and pathological human nerves", Muscle & nerve, vol. 29, No. 4 (2004), pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, 53, No. 4, 1999, pp. 871-874.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott, "The Electrode-Tissue Interface During Recording and Stimulation in the Central Nervous System", published on May 2010.

Levy et al., "Incidence and Avoidance of Neurologic Complications with Paddle Type Spinal Cord Stimulation Leads", Neuromodulation 14(15), Sep. 2011, pp. 412-422.

Li et al., S, "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Macefield, "Spontaneous and Evoked Ectopic Discharges Recorded from Single Human Axons", Muscle & Nerve 21, No. 4, Apr. 1998, pp. 461-468.

Markandey, Vishal, "ECG Implementation on the TMS320C5515 DSP Medical Development Kit (MDK)", Texas Instruments Application Report Jun. 2010, 35 pgs.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445 1982.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.

(56) References Cited

OTHER PUBLICATIONS

Oakley et al., "Spinal Cord Stimulation: Mechanisms of Action", Spine 27, No. 22, Nov. 15, 2002, pp. 2574-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Oh et al., "Long-term hardware-related complications of deep brain stimulation", Neurosurgery, vol. 50, No. 6, Jun. 2002, pp. 1268-1274, discussion pp. 1274-1276.

Parker et al., "Closing the Loop in Neuromodulation Therapies: Spinal Cord Evoked Compound Action Potentials During Stimulation for Pain Management (230)", 2011, In 15th Annual Meeting, North American Neuromodulation Society (p. 48). Presented at the North American Neuromodulation Society, Las Vegas.

Parker et al., "Compound action potentials recorded in the human spinal cord during neurostimulation for pain relief", Pain, 2012, vol. 153, pp. 593-601.

Parker et al., "Electrically Evoked Compound Action Potentials Recorded From the Sheep Spinal Cord", Neuromodulation, vol. 16, 2013, pp. 295-303.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.15251403.2011.00352.x.

Ridder et al., "Burst Spinal Cord Stimulation for Limb and Back Pain", World Neurosurgery, 2013, 9 pgs.

Ridder et al., "Burst Spinal Cord Stimulation toward Paresthesia-Free Pain Suppression", May 2010, vol. 66, pp. 986-990.

Schmidt et al., "Gating of tactile input from the hand", Exp Brain Res, 1990, 79, pp. 97-102.

Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.

Siegfried et al., "Intracerebral Electrode Implantation System", Journal of Neurosurgery, vol. 59, No. 2, Aug. 1983, pp. 356-3591.

Srinivasan, S, "Electrode/Electrolyte Interfaces: Structure and Kinetics of Charge Transfer", Fuel Cells, 2006, Chapter 2, 67 Pages.

Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.

Sufka et al., "Gate Control Theory Reconsidered", Brain and Mind, 3, No. 2, 2002, pp. 277-290.

Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.

Tasker, "Deep Brain Stimulation is Preferable to Thalamotomy for Tremor Suppression", Surgical Neurology, 49, No. 2, 1998, pp. 145-153.

Taylor et al., "Spinal Cord Stimulation for Chronic Back and Leg Pain and Failed Back Surgery Syndrome: A Systematic Review and Analysis of Prognostic Factors", Spine, vol. 30, No. 1, pp. 152-160.

Texas Instruments, "Precision, Low Power Instrumentation Amplifiers", Texas Instruments SBOS051B Oct. 1995, Revised Feb. 2005, 20 pgs.

Tscherter et al., "Spatiotemporal Characterization of Rhythmic Activity in Rat Spinal Cord Slice Cultures", European Journal of Neuroscience 14, No. 2 (2001), pp. 179-190.

Van Den Berg et al., "Nerve fiber size-related block of action currents by phenytoin in mammalian nerve", Epilepsia, Nov. 1994, 35(6), pp. 1279-1288.

Villavicencio, Alan T., "Laminectomy versus Percutaneous Electrode Placement for Spinal Cord Stimulation," Neurosurgery, vol. 46 (2), Feb. 2000, pp. 399-405.

Vleggeert et al., Lankamp, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.

Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.

Xie et al., "Functional Changes in Dorsal Root Ganglion Cells after Chronic Nerve Constriction in the Rat", Journal of Neurophysiology 73, No. 5 (May 1, 1995): 1811-1820.

Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.

Yingling et al., "Use of Antidromic Evoked Potentials in Placement of Dorsal Cord Disc Electrodes", Applied Neurophysiology, 1986, vol. 49, pp. 36-41. Whole Document.

* cited by examiner

METHOD AND APPARATUS FOR APPLICATION OF A NEURAL STIMULUS

CROSS-REFERENCE TO RELATED APPLICATIONS

This application is a continuation of U.S. patent application Ser. No. 14/117,586, filed on Nov. 13, 2013, which is a U.S. National Stage Application under 35 U.S.C. § 371 of International Application No. PCT/AU2012/000515, filed on May 11, 2012, which claims priority to Australian Provisional Patent Application No. AU2011901828 filed May 13, 2011 and Australian Provisional Patent Application No. AU2011901829 filed May 13, 2011, all of which are incorporated herein by reference.

TECHNICAL FIELD

The present invention relates to application of a neural stimulus, and in particular relates to applying a neural stimulus in a controlled manner by using one or more electrodes implanted proximal to the neural pathway.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Ai fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of applying a neural stimulus with an implanted electrode array, the method comprising:

using the electrode array to applying a sequence of stimuli configured to yield a therapeutic effect while suppressing psychophysical side effects, the stimuli sequence configured such that a first stimulus recruits a portion of the fibre population, and a second stimulus is delivered within the refractory period following the first stimulus and the second stimulus being configured to recruit a further portion of the fibre population.

According to a second aspect the present invention provides a device for applying a neural stimulus, the device comprising:

at least one electrode configured to be positioned alongside a neural pathway; and a control unit configured to apply a sequence of neural stimuli which are configured to yield a therapeutic effect while suppressing psychophysical side effects, the stimuli sequence configured such that a first stimulus recruits a portion of the fibre population, and a second stimulus is delivered within the refractory period following the first stimulus and the second stimulus being configured to recruit a further portion of the fibre population.

By providing for a second stimulus to be delivered in the neural refractory period following the first stimulus, the present invention provides for de-correlated, or less correlated, fibre responses to be evoked by such stimuli.

The sequence of neural stimuli may comprise more than two stimuli, each being delivered in the refractory period following a previous stimulus in the sequence.

The sequence of neural stimuli may comprise stimuli of ascending amplitude.

The sequence of neural stimuli may be applied sequentially by a single electrode.

Alternatively, the sequence of neural stimuli may be applied sequentially by more than one electrode. In such embodiments, the second stimulus is preferably delivered at a time after the first stimulus which allows for cessation of the first stimulus and allows for propagation of a first neural response evoked by the first stimulus from the first electrode to the second electrode, so that the second stimulus is delivered during a refractory period of neurons proximal to the second electrode after activation of those neurons by the evoked neural response from the first stimulus.

Additionally or alternatively, in some embodiments the sequence of neural stimuli may be applied by consecutive electrodes positioned along an electrode array.

In embodiments where the sequence of neural stimuli is applied sequentially by more than one electrode, the timing of the respective stimuli in the sequence may be controlled in order to cause spatiotemporal alignment of the respective evoked responses propagating in a first direction along the nerve fibre to thereby cause correlation and summation of evoked responses in the first direction, while causing spatiotemporal misalignment of the respective evoked responses propagating in a second direction opposite the first direction along the nerve fibre, to thereby decorrelate evoked responses propagating in the second direction. Such embodiments may be advantageous in decorrelating evoked potentials propagating toward the brain, where it is desired to avoid or minimise any percept from the stimuli.

In some embodiments of the invention, the sequence of neural stimuli may be followed by a single stimulus which is not applied during the refractory period of any preceding stimulus, and which is not closely followed by any subsequent stimulus in the refractory period of the single stimulus. Such embodiments may be applied in order to enable an evoked response measurement to be made following the single stimulus, to enable ongoing refinement of stimulus parameters of the sequence of neural stimuli.

According to another aspect the present invention provides a computer program product comprising computer program code means to make a computer execute a procedure for applying a neural stimulus with an implanted electrode array, the computer program product comprising computer program code means for carrying out the method of the first aspect.

BRIEF DESCRIPTION OF THE DRAWINGS

An example of the invention will now be described with reference to the accompanying drawings, in which:

FIG. 2a shows the Aβ response amplitude growth functions for stimulation of the sheep spinal cord at 40, 80 and 120 μs, while

DESCRIPTION OF THE PREFERRED EMBODIMENTS

Figure 1:
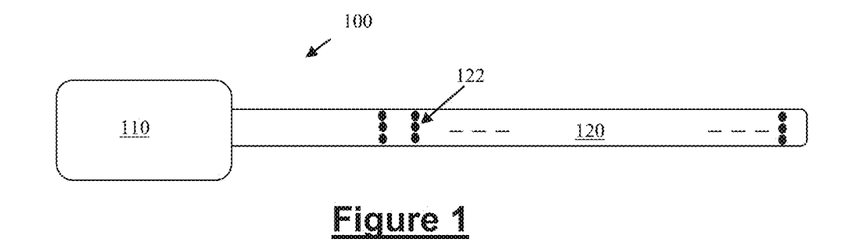
FIG. 1 illustrates an implantable device suitable for implementing the present invention.

FIG. 1 illustrates an implantable device 100 suitable for implementing the present invention. Device 100 comprises an implanted control unit 110, which controls application of a sequence of neural stimuli in accordance with the present invention. In this embodiment the unit 110 is also configured to control a measurement process for obtaining a measurement of a neural response evoked by a single stimulus delivered by one or more of the electrodes 122. Device 100 further comprises an electrode array 120 consisting of a three by eight array of electrodes 122, each of which may be selectively used as either the stimulus electrode or sense electrode, or both.

The activation and simultaneous suppression of different areas of tissue is highly desired for treatment of a number of neurological disorders. The activation of micturition or defection without contraction of the sphincter is highly desirable for treatment of incontinence. The goal of stimulation of the spinal cord is to block transmission of pain signals from Aδ and C fibres, via the inhibitory effect of the activation of Aβ fibres. The ascending Aβ fibres produce a psycho-physiological response which results in the paraesthesia (described as tingling by recipients). A number of ways to reduce or eliminate this effect have been suggested. It has been reported that burst mode stimulation or continuous stimulation at high frequencies can produce pain relief without accompanying paraesthesia, however the mechanisms are not clear.

One possible explanation is that the high frequency stimulation results in a highly uncorrelated neural firing pattern in the ascending Aβ tracts. High frequency stimulation results in the continuous activation of the fibres and produces a randomised firing pattern. The recovery time (refractory period) between each fibre is slightly different and if a depolarisation potential is present as the fibre comes out of refractory period, it will depolarise again, but not synchronised with other fibres which may still be in their refractory periods. The net result is a randomisation of the firing pattern and a return of the stochastic response in the fibre.

Figure 2A:
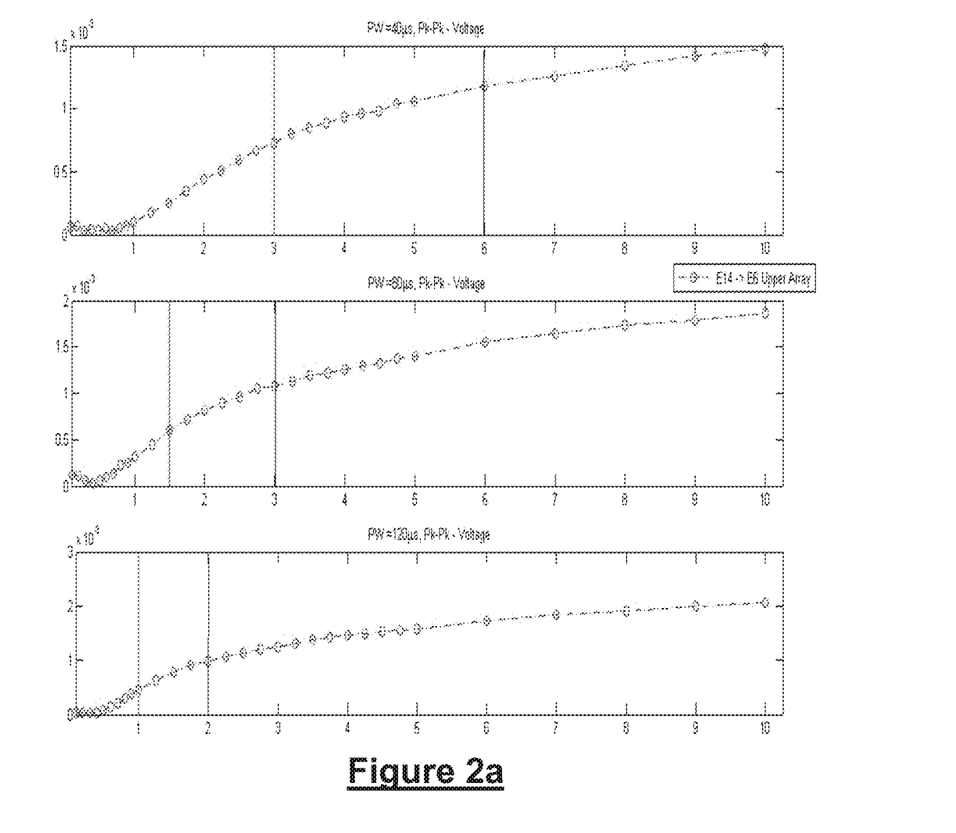
Figure 2B:
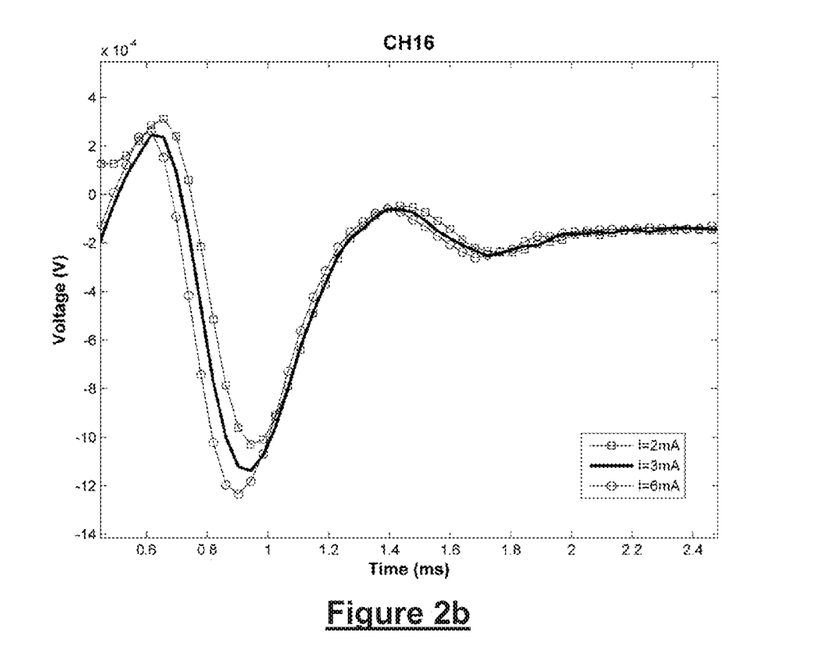
FIG. 2b shows the compound action potential recorded at equivalent charges for the three different pulse widths.

Measurements of the evoked neural response provide a direct measure of the degree of correlation of the firing pattern. FIG. 2a shows the Aβ response amplitude growth functions with respect to stimulus amplitude, for stimulation of the sheep spinal cord at 40, 80 and 120 μs. The recruitment is related to charge and so stimulation at 1 mA for 120 μs produces an equivalent charge for stimulation at 3 mA for 40 μs, with vertical lines highlighting two respective points of equal charge delivery for each trace. FIG. 2b shows the compound action potential recorded at equivalent charges for the three different pulse widths. The peak height is smaller and the evoked response peak is wider at the equivalent charge for the longer pulse width than for the shorter pulse width, and this is indicative of a less correlated evoked response.

The probability of any single fibre responding is a function of the properties and history of the fibre and the amplitude of the current pulse. Although short and long pulses for an equivalent charge may recruit the same number of fibres the longer lower current amplitude pulse will recruit the fibres over a longer time scale than the higher current shorter pulse width.

Patients report a preference for stimulation with longer pulse widths and the reason for this preference may be because the perceptual side effect is lower, because there is a lower correlation between the fibres firing. Given this observation, highly uncorrelated responses may give rise to much lower psycho-physical side effects such as tingling sensations and paraesthesia. The evoked responses measured for the longer pulse widths are broader in FIG. 2b, indicating less correlation in the firing pattern.

Measurement of the evoked response provides a unique way to assess the degree of correlation amongst fibres in a group, as the peak width and amplitude of the measured response directly relates to the degree of timing synchronisation of the single fibre action potentials which sum to form the compound action potential. The goal of stimulus design is to achieve a high level of recruitment at the segmental level and a low level of correlation for the ascending segments. The neural response measurement obtained at each sense electrode may be conducted in accordance with the techniques set out in Daly (2007/0225767), the content of which is incorporated herein by reference. Additionally or alternatively, the neural response measurement may be conducted in accordance with the techniques set out in Nygard (U.S. Pat. No. 5,785,651), the content of which is incorporated herein by reference. Additionally or alliteratively, the neural response measurement may be conducted in accordance with the techniques set out in the Australian provisional patent application filed simultaneously herewith in the name of National ICT Australia Ltd entitled "Method and apparatus for measurement of neural response".

The degree of correlation within an evoked response can be measured with such techniques, and pulse sequences can be designed to produce evoked responses of a desired character. A typical recruitment curve is shown in FIG. 2a.

The strength of the Aβ potentials directly relates to the number of fibres recruited, and therefore stimulation at successive larger and larger pulse amplitudes will recruit successively more fibres. If the pulses are timed so that they occur within the refractory period of the excited neurons from the previous pulse then different sub populations of neurons can be selected with each pulse.

The timing of each pulse can be so arranged so that the travelling CAPs from each individual pulse cancel each other as they sum at some distance from the stimulation site. This indicates the degree of desynchronisation between the fibres, and as the sensory input is based on correlation of firing patterns the sensation (paraesthesia) is reduced. However, the activation of the inhibitory effect of the Aβ fibres at the segmental level is not reduced, permitting Aβ inhibition of Ai and C propagation to occur, as desired.

Figure 3:
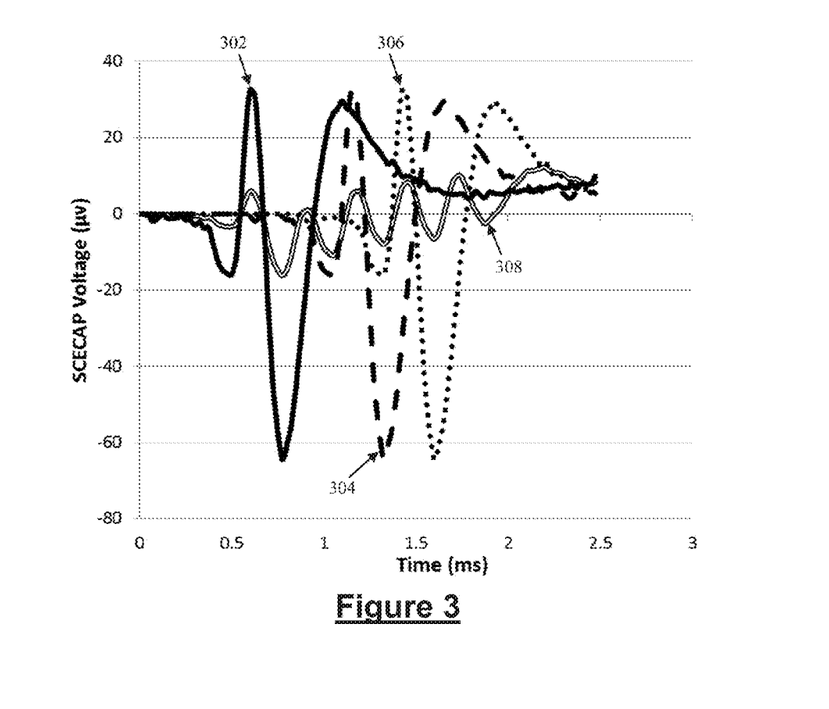
FIG. 3 illustrates summation of a sequence of overlapped neural responses.

FIG. 3 illustrates the principle of applying a sequence of neural stimuli and allowing the respective evoked responses 302, 304, 306 to propagate along the fibre. The numerical summation of five such partially overlapping compound action potentials, of which only three appear in FIG. 3, is shown at 308. FIG. 3 shows the effect of the summation of the evoked response from five pulses with the timing intervals between the pulses so arranged as result in the arrival of the evoked response waveform at a designated point along the electrode array such that the averaged signal recorded at that point is minimised. For the data shown in FIG. 3 the timing difference between each cathodic pulse is 0.3 ms.

Figure 4:
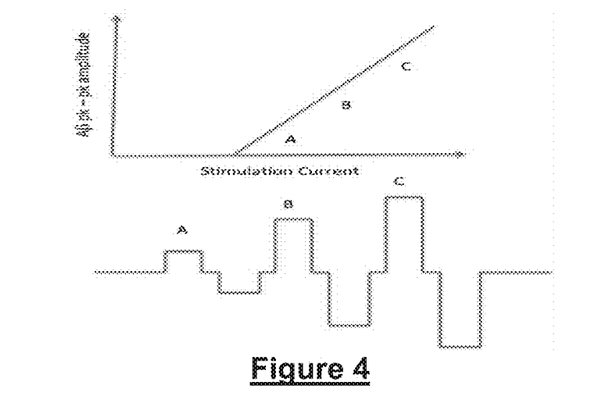
FIG. 4 is a schematic illustration of a potential pulse sequence and the amplitude growth curve associated with the sequence.

FIG. 4 is a schematic illustration of a potential pulse sequence (lower) and the amplitude growth curve associated with the sequence (upper). Current levels A-C are represented on both portions of FIG. 4. The initial pulse of amplitude A can be expected to recruit only a portion of the available population. Application of the subsequent stimulus of greater amplitude can then be expected to recruit a further portion, but not all, of the available neural population, even though stimulus B is applied during the refractory period after stimulus A. Similarly, stimulus C can be expected to recruit a further portion of the available neural population. C may be applied during the refractory period of stimulus B only, or possibly within the refractory period of both stimuli A and B. The sequence of neural stimuli A-B-C can thus be expected to recruit perhaps a similar amount of the available neural population as would stimulus C if applied alone, however the progressive recruitment of portions of the neural population at progressive times provides for a significantly decorrelated evoked response as compared to the response resulting from a single stimulus of amplitude C.

The concept of a selection of stimulus sequences based on the ERT recorded parameters can be greatly extended. For instance the example of FIG. 4 demonstrates achieving an uncorrelated ensemble response in the fibre population being stimulated.

Figure 5:
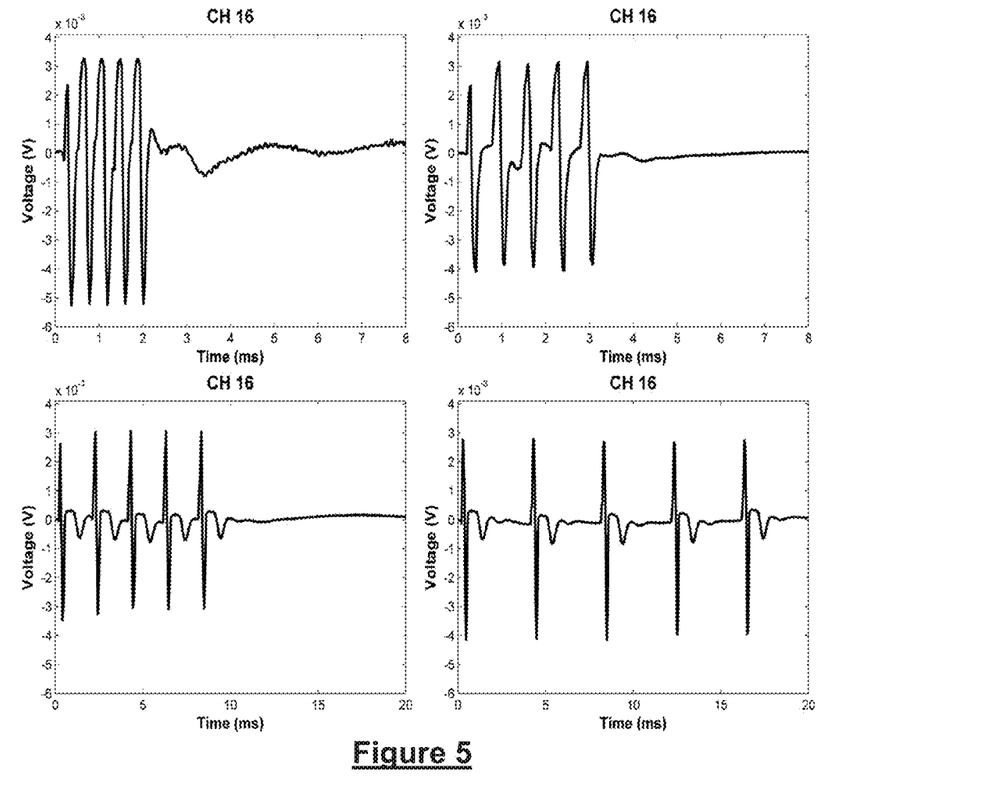
FIG. 5 illustrates ERT responses to bursts of stimulation with differing frequencies.

FIG. 5 illustrates ERT responses to bursts of stimulation with differing frequencies. The degree of correlation can be inferred from the ERT signal. A normal stimulus can be used to assess the stimulation response amplitude in the absence of any further desynchronising pulses. The amplitude of the single probe pulse is adjusted to represent the total charge delivered over time for the corresponding desynchronising pulse train. The amplitude of the response measured from the single probe pulse represents a fully synchronised response. The desynchronising pulse train is then output and the response measured. The ratio of the two responses is proportional to the level of synchronisation and so can be used as a control parameter for adjusting the characteristics of the device. For instance the control parameter may be adjustable by the patient to allow the patient to adjust the level of perceived paraesthesia. The control variable may also be used by the system for detection of a change of state in the neural tissue for a diagnostic purpose.

A single non-decorrelating stimulus can be applied to the nerve by the device periodically or occasionally in order to elicit an evoked response which is then used as the input to the control loop. This probe stimulus can be adjusted so that its charge is equivalent to the charge presented by the desynchronising stimuli. The frequency of the probe pulse to desynchronising pulses can then be adjusted to minimise the perceptual side effects. The probe frequency can also be adjusted on demand, responding more rapidly to changes in movement, for example.

Figure 6:
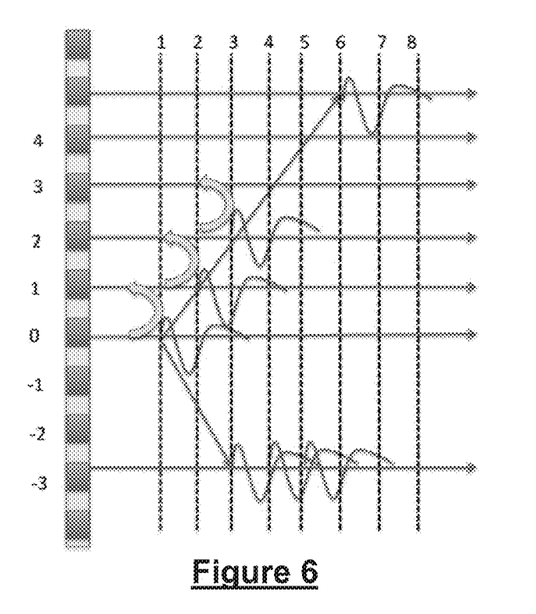
FIG. 6 illustrates a stimuli scheme to generate stimuli which result in synchronising Aβ activation in the antidromic direction and a desynchronising activity in the orthodromic direction.

Conduction of the compound action potentials occurs both orthodromically (up the spine) and antidromically (down the spine). Careful choice of stimulus design can be used to create a situation where the degree of synchronisation can be different in both directions, and controllably so. For example it may be desirable to generate stimuli which result in synchronising Aβ activation in the antidromic direction and a desynchronising activity in the orthodromic direction. One possible scheme for doing this is illustrated in FIG. 6. A stimulus pulse, preferably biphasic, is discharged at an electrode (electrode '0' indicated on the left side of FIG. 6). At some time interval later a $2^{nd}$ stimulus pulse is discharged between another two electrodes. For convenience this is illustrated in FIG. 6 as the electrode (number "1") adjacent to the first electrode. The $2^{nd}$ discharge is arranged so that it occurs in time and place such that its resultant CAP propagation to an electrode (e.g. '+6') in one direction (the upward direction in FIG. 6) sums with each other evoked CAP. In contrast, in the other direction (the downward direction in FIG. 6), the respective CAPs are misaligned and decorrelated for example when observed at electrode '−3'.

A possible means but not the only means to achieve such directional selectivity of CAP correlation is to arrange a series of stimulus pulses with an interpulse interval equal to the difference in propagation time required for desynchronisation of the CAP in the ascending direction.

Note that the order in which the stimuli are presented does not need to be sequential. The amplitudes of the individual stimuli can also be varied according to the scheme of FIG. 4. The timing of presentation can also be dithered to adjust the timing.

Figure 7:
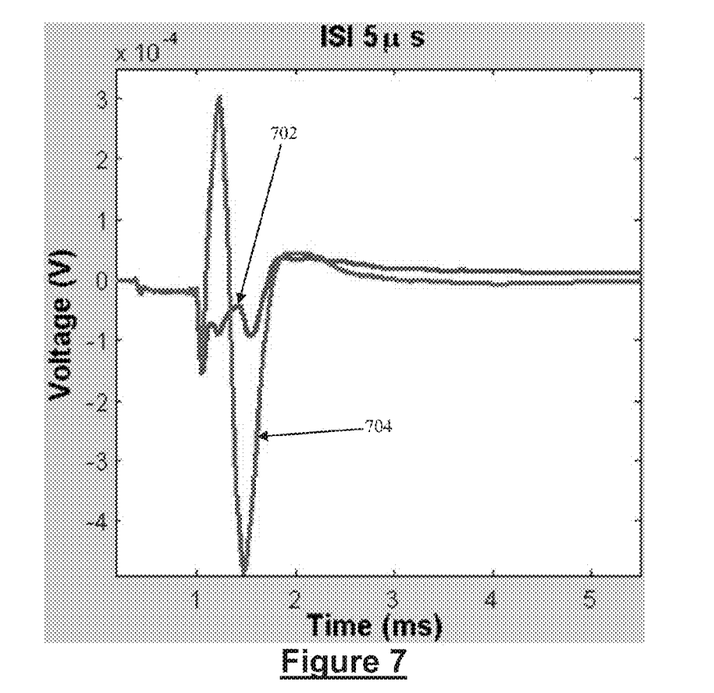
FIG. 7 illustrates experimental results obtained by applying a series of four stimuli of ascending amplitude on four adjacent electrodes to a sheep spinal cord.

FIG. 7 illustrates experimental results obtained by applying a series of four stimuli of ascending amplitude on four adjacent electrodes to a sheep spinal cord. Each stimulus was a tripolar stimulus for which the respective centre electrode was, in order, electrode E7, E8, E9 and E10, being the four centrally positioned electrodes of a 16 electrode linear electrode array. Each stimulus was biphasic with each phase having a pulse width of 20 µs, and the interphase gap being 10 µs. The stimuli were of ascending amplitude, being 2 mA, 2.5 mA, 3 mA and 3.5 mA respectively. The inter-stimulus interval between each successive pair of stimuli on the respective electrodes was 33 µs, so that the pulse-to-pulse time was 83 µs, to optimally correlate the net evoked response in the antidromic (ie caudal) direction. As can be seen in FIG. 7 the antidromic response 704 measured on electrode E16 was well correlated from the four constituent parts, and is of large amplitude. In contrast, the four orthodromic responses were effectively decorrelated and produced a net response 702 measured at electrode E3 which was of much reduced amplitude compared to response 704 travelling in the opposite direction, even though both were produced by the same burst of four stimuli.

Figure 8:
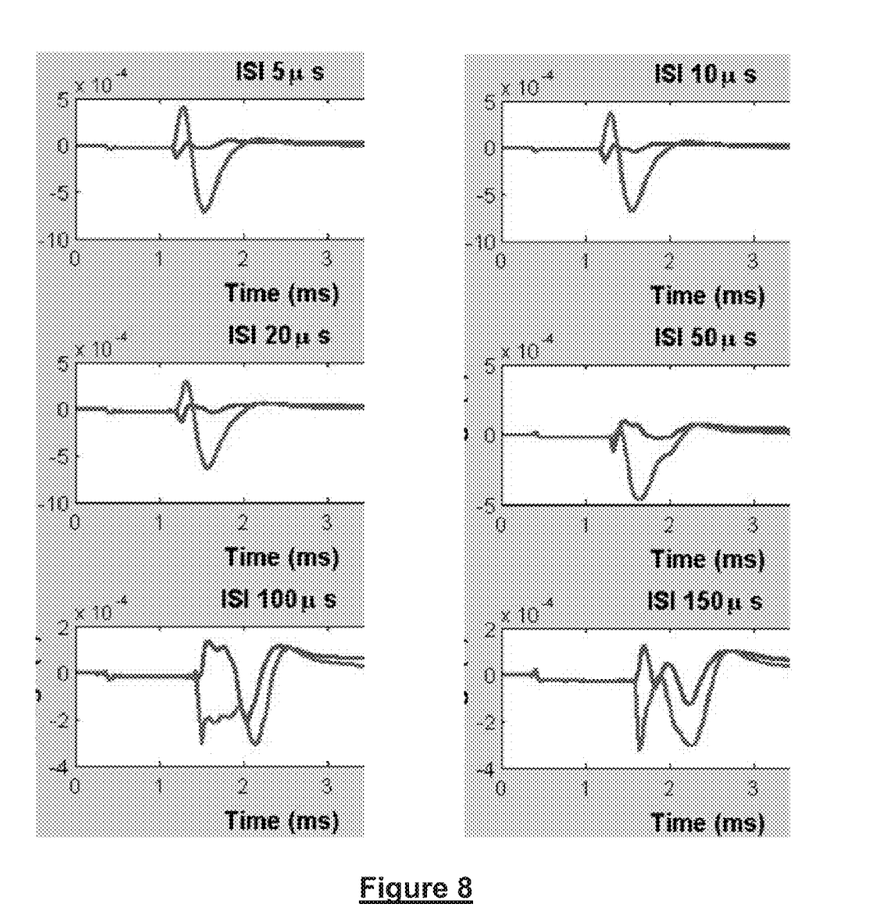
FIG. 8 illustrates experimental results obtained in response to stimuli bursts of different inter-stimulus intervals.
Figure 9:
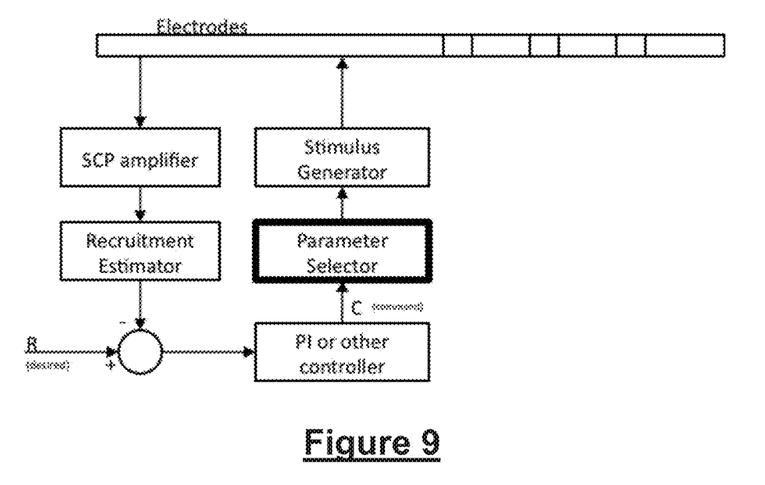
FIG. 9 illustrates a suitable feedback controller for controlling the parameters of the stimuli burst in an automated manner.

FIG. 8 shows the responses measured at different inter-stimulus intervals. As can be seen the inter-stimulus interval strongly affects efficacy of this technique, and so preferred embodiments provide a feedback loop in order to optimize this parameter, and all other stimulus parameters, in setting up the stimuli burst. FIG. 9 illustrates a suitable feedback controller for controlling the parameters of the stimuli burst in an automated manner, so as to use the measured evoked responses in each direction to determine the stimulus parameters required to achieve a desired directional effect. Such automated feedback permits the relatively large parameter space to be efficiently explored to identify optimal stimuli burst parameters.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of applying a neural stimulus with an implanted electrode array, the method comprising:
using a first electrode of the electrode array to apply a sequence of stimuli configured to yield a therapeutic effect while suppressing psychophysical side effects, the stimuli sequence configured such that a first stimulus applied by the first electrode recruits a portion of the fibre population, and a second stimulus applied by the first electrode is delivered within the refractory period following the first stimulus and the second stimulus being configured to recruit a further portion of the fibre population, so as to reduce a correlation of an action potential volley across the stimulated fibre population in order to produce a reduced perceived sensation of stimulation, and wherein a further sequence of neural stimuli is applied sequentially by more than one electrode, the further sequence comprising a further stimulus which is delivered by a second electrode at a time after the first stimulus which allows for cessation of the first stimulus and allows for propagation of a first neural response evoked by the first stimulus from the first electrode to the second electrode, so that the second stimulus is delivered by the second electrode during a refractory period of neurons proximal to the second electrode after activation of those neurons by the evoked neural response from the first stimulus.

2. The method of claim 1 wherein the sequence of neural stimuli comprises more than two stimuli, each being delivered by the first electrode in the refractory period following a previous stimulus in the sequence.

3. The method of claim 1 wherein the sequence of neural stimuli comprises stimuli of ascending amplitude.

4. The method of claim 1 wherein the sequence of neural stimuli comprises stimuli of ascending charge.

5. The method of claim 1 wherein the further sequence of neural stimuli is applied by consecutive electrodes positioned along the electrode array.

6. The method of claim 1 further comprising applying a stimulus which is not applied during the refractory period of any preceding stimulus, and which is not closely followed by any subsequent stimulus in the refractory period of the single stimulus, in order to enable an evoked response measurement to be made following the single stimulus.

7. The method of claim 6 further comprising using the evoked response measurement for feedback control of stimulus parameters of the sequence of neural stimuli.

8. A device for applying a neural stimulus, the device comprising:
- at least a first electrode configured to be positioned alongside a neural pathway; and
- a control unit configured to apply a sequence of neural stimuli which are configured to yield a therapeutic effect while suppressing psychophysical side effects, the stimuli sequence configured such that a first stimulus delivered by the first electrode recruits a portion of the fibre population, and a second stimulus is delivered by the first electrode within the refractory period following the first stimulus and the second stimulus being configured to recruit a further portion of the fibre population, so as to reduce a correlation of an action potential volley across the stimulated fibre population in order to produce a reduced perceived sensation of stimulation, and wherein a further sequence of neural stimuli is applied sequentially by more than one electrode, the further sequence comprising a further stimulus which is delivered by a second electrode at a time after the first stimulus which allows for cessation of the first stimulus and allows for propagation of a first neural response evoked by the first stimulus from the first electrode to the second electrode, so that the second stimulus is delivered by the second electrode during a refractory period of neurons proximal to the second electrode after activation of those neurons by the evoked neural response from the first stimulus.

9. The device of claim 8 wherein the sequence of neural stimuli comprises more than two stimuli, each being delivered by the first electrode in the refractory period following a previous stimulus in the sequence.

10. The device of claim 8 wherein the sequence of neural stimuli comprises stimuli of ascending amplitude.

11. The device of claim 8 wherein the sequence of neural stimuli comprises stimuli of ascending charge.

12. The device of claim 8 wherein the further sequence of neural stimuli is applied by consecutive electrodes positioned along the electrode array.

13. The device of claim 8 wherein the control unit is further configured to apply a stimulus which is not applied during the refractory period of any preceding stimulus, and which is not closely followed by any subsequent stimulus in the refractory period of the single stimulus, in order to enable an evoked response measurement to be made following the single stimulus.

14. The device of claim 13 further comprising using the evoked response measurement for feedback control of stimulus parameters of the sequence of neural stimuli.

* * * * *